(12) United States Patent
Cifuentes-Garcia et al.

(10) Patent No.: US 11,655,214 B2
(45) Date of Patent: May 23, 2023

(54) PHENYL-2-HYDROXY-ACETYLAMINO-2-METHYL-PHENYL COMPOUNDS FOR THE TREATMENT OF PANCREATIC CANCER

(71) Applicant: ELI LILLY AND COMPANY, Indianapolis, IN (US)

(72) Inventors: Marta Maria Cifuentes-Garcia, Indianapolis, IN (US); Maria Cristina Garcia Paredes, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 52 days.

(21) Appl. No.: 16/606,410

(22) PCT Filed: Apr. 11, 2018

(86) PCT No.: PCT/US2018/027005
§ 371 (c)(1),
(2) Date: Oct. 18, 2019

(87) PCT Pub. No.: WO2018/194885
PCT Pub. Date: Oct. 25, 2018

(65) Prior Publication Data
US 2021/0114985 A1    Apr. 22, 2021

(30) Foreign Application Priority Data

Apr. 18, 2017 (EP) .................................... 17382207

(51) Int. Cl.
| | | |
|---|---|---|
| *A61K 31/167* | (2006.01) | |
| *C07C 233/01* | (2006.01) | |
| *C07D 213/82* | (2006.01) | |
| *A61P 35/00* | (2006.01) | |
| *C07D 241/28* | (2006.01) | |
| *C07D 487/04* | (2006.01) | |

(52) U.S. Cl.
CPC ............ *C07D 213/82* (2013.01); *A61P 35/00* (2018.01); *C07D 241/28* (2013.01); *C07D 487/04* (2013.01)

(58) Field of Classification Search
CPC ........................... A61K 31/167; C07C 233/01
USPC ........................................... 514/622; 564/192
See application file for complete search history.

(56) References Cited

U.S. PATENT DOCUMENTS

| | | |
|---|---|---|
| 2003/0187001 A1 | 10/2003 | Calderwood et al. |
| 2010/0167945 A1 | 7/2010 | Singh et al. |
| 2013/0018038 A1 | 1/2013 | Axten et al. |
| 2017/0022206 A1 | 1/2017 | Hodous et al. |
| 2019/0241573 A1 | 8/2019 | Axten et al. |
| 2019/0388426 A1 | 12/2019 | Nguyen et al. |
| 2020/0031834 A1 | 1/2020 | Bartlett et al. |

FOREIGN PATENT DOCUMENTS

| | | |
|---|---|---|
| CN | 106748989 A | 5/2017 |
| EP | 3067356 A1 | 9/2016 |
| EP | 3492454 A1 | 6/2019 |
| WO | WO-98/41525 A1 | 9/1998 |
| WO | WO-2003064397 A1 | 8/2003 |
| WO | WO-03/093297 A2 | 11/2003 |
| WO | WO-2005009961 A2 | 2/2005 |
| WO | WO-2007026920 A2 | 3/2007 |
| WO | WO-2007030377 A1 | 3/2007 |
| WO | WO-2010/080992 A1 | 7/2010 |
| WO | WO-2014/170706 A1 | 10/2014 |
| WO | WO-2015/056180 A1 | 4/2015 |
| WO | WO-2015136463 A1 | 9/2015 |
| WO | WO-2016/004254 A1 | 1/2016 |
| WO | WO-2016/075224 A1 | 5/2016 |
| WO | WO-2016/185160 A1 | 11/2016 |
| WO | WO-2018/009017 A1 | 1/2018 |
| WO | WO-2018/138358 A1 | 8/2018 |
| WO | WO-2018/194885 A1 | 10/2018 |
| WO | WO-2019/099564 A1 | 5/2019 |
| WO | WO-2019/191115 A1 | 10/2019 |
| WO | WO-2020/070053 A1 | 4/2020 |

OTHER PUBLICATIONS

Belikov, V.G., Pharmacutical Chemistry, 4th Ed., Medpress-inform, 622:11 (2007) with English translation (13 pages total).
International Search Report and Written Opinion in PCT/US2018/027005, dated Jun. 19, 2018 8 pages.
Kummerer, K., "Pharmaceuticals in the Environment," Ann. Rev. Environ. Res., 35:57-75 (2010).
Atkins C, Liu Q, Minthorn E, et al. Characterization of a novel PERK kinase inhibitor with antitumor and antiangiogenic activity. Cancer Res. 2013;73: 1993-2002.
Avivar-Valderas A, Salas E, Bobrovnikova-Marjon E, et al. PERK integrates autophagy and oxidative stress responses to promote survival during extracellular matrix detachment. Mol Cell Biol. 2011;31(17):3616-3629.
Avivar-Valderas A, Bobrovnikova-Marjon E, Alan Diehl J, Bardeesy N, Debnath J, Aguirre-Ghiso JA. Regulation of autophagy during ECM detachment is linked to a selective inhibition of mTORC1 by PERK. Oncogene. 2013;32(41):4932-4940.

(Continued)

*Primary Examiner* — Douglas M Willis
(74) *Attorney, Agent, or Firm* — Goodwin Procter LLP

(57) ABSTRACT

The present invention provides phenyl-2-hydroxy-acetylamino-2-methyl-phenyl compounds, such as compounds of formula I:

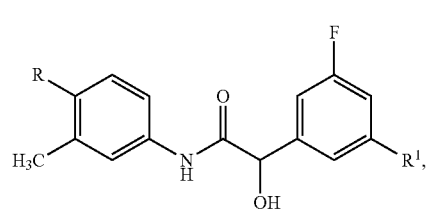

pharmaceutical compositions comprising the compounds, and methods of using the compounds to treat physiological disorders such as pancreatic cancer.

10 Claims, No Drawings

(56) References Cited

OTHER PUBLICATIONS

Bi M, Naczki C, Koritzinsky M, et al. ER stress-regulated translation increases tolerance to extreme hypoxia and promotes tumor growth. EMBO J. 2005;24(19):3470-3481.

Blais JD, Filipenko V, Bi M, et al. Activating transcription factor 4 is translationally regulated by hypoxic stress. Mol Cell Biol. 2004;24(17):7469-7482.

Cella, D. Quality of life in patients with metastatic renal cell carcinoma: The importance of patient-reported outcomes. Cancer Treat Rev. 2009;35:733-737.

Chen X, Iliopoulos D, Zhang Q, et al. XBP1 promotes triple-negative breast cancer by controlling the HIF1 α pathway. Nature. 2014;508(7494):103-107.

Chevet E, Hetz C, Samali A. Endoplasmic reticulum stress-activated cell reprogramming in oncogenesis. Cancer Discov. 2015;5(6):586-597.

Choueiri TK, Motzer RJ. Systemic Therapy for Metastatic Renal-Cell Carcinoma. N Engl J Med. 2017;376(4):354-366.

Chow W.H., Devesa S.S., Warren J.L., Fraumeni J.F. Rising incidence of renal cell cancer in the United States. JAMA. 1999;281(17):1628-1631.

De Groot S, Redekop Wek, Verstegh MM, et al. Health-related quality of life and its determinants in patients with metastatic renal cell carcinoma. Qual Life Res. 2018;27:115-124.

Dey S, Sayers CM, Verginadis II, et al. ATF4-dependent induction of heme oxygenase 1 prevents anoikis and promotes metastasis. J Clin Invest. 2015;125(7):2592-2608.

Diamond E, Molina AM, Carbonaro M, et al. Cytotoxic chemotherapy in the treatment of advanced renal cell carcinoma in the era of targeted therapy. Critical Review Oncol Hematol. 2015;96:518-526.

Escudier B, Eisen T, Porta C, et al. Renal cell carcinoma: ESMO Clinical Practice Guidelines for diagnosis, treatment and follow-up. Ann Oncol. 2012;23(suppl 7):vii65-vii71.

Escudier B, Eisen T, Stadler WM, et al. Sorafenib in advanced clear-cell renal-cell carcinoma. N Engl J Med. 2007;356:125-134.

Feng YX, Jin DX, Sokol ES, et al. Cancer-specific PERK signaling drives invasion and metastasis through CREB3L1. Nat Commun. 2017;8(1):1-10.

Feng YX, Sokol ES, Del Vecchio CA, et al. Epithelial-to-mesenchymal transition activates PERKeIF2α and sensitizes cells to endoplasmic reticulum stress. Cancer Discov. 2014;4(6):702-715.

Ferlay J, Ervik M, Lam F, et al. Global Cancer Observatory: Cancer Today. Lyon: International Agency for Research on Cancer; 2020.

Fusco V, Parisi S, d'Andrea B, et al. Role of radiotherapy in the treatment of renal cell cancer: updated and critical review. 2017; 103(6):504-510.

Guidance for Industry, Estimating the Maximum Safe Starting Dose in Initial Clinical Trials for Therapeutics in Adult Healthy Volunteers. U.S. Department of Health and Human Services, Food and Drug Administration, Center for Drug Evaluation and Research (CDER), Jul. 2005.

Han KS, Li N, Raven PA, et al. Inhibition of endoplasmic reticulum chaperone protein glucoseregulated protein 78 potentiates anti-angiogenic therapy in renal cell carcinoma through inactivation of the PERK/elF2α pathway. Oncotarget. 2015;6(33):34818-34830.

Harding HP, Zhang Y, Ron D. Protein translation and folding are coupled by an endoplasmicreticulum-resident kinase. Nature. 1999;397(6716):271-274.

Hart LS, Cunningham JT, Datta T, et al. ER stress-mediated autophagy promotes Myc-dependent transformation and tumor growth. J Clin Invest. 2012;122(12):4621-4634.

Hsieh JJ, Purdue MP, Signoretti S, et al. Renal cell carcinoma. Nat Rev Dis Primers. 2017; 3:17009.

Iriyama N, Hino H, Moriya S, et al. The cyclin-dependent kinase 4/6 inhibitor, abemaciclib, exerts dose-dependent cytostatic and cytocidal effects and induces autophagy in multiple myeloma cells. Leuk Lymphoma. 2018;59(6):1439-1450.

Janowitz T, Welsh SJ, Zaki K, et al. Adjuvant therapy in renal cell carcinoma-past, present, and future. Semin Oncol. 2013;40(4):482-91.

Kamii H, Li L, Gobe GC. Limitations to the Therapeutic Potential of Tyrosine Kinase Inhibitors and Alternative Therapies for Kidney Cancer. Ochsner J. 2019;19:138-151.

Ko JJ, Choueiri TK, Rini BI, et al. First-, second-, third-line therapy for mRCC: benchmarks for trial design from the IMDC. Br J Cancer. 2014;110(8):1917-22.

Kotecha RR, Motzer RJ, Voss MH. Towards individualized therapy for metastatic renal cell carcinoma Nat Rev Clin Oncol. 2019;16(10):621-633.

Kuo CY, Lin CH, Hsu T, et al. VHL inactivation in precancerous kidney cells induces an inflammatory response via ER stress-activated IRE1a signaling. Cancer Res. 2017;77(13):3406-3416.

Lane BR, Tobert CM, Riedinger CB. Growth kinetics and active surveillance for small renal masses. Curr Opin Urol. 2012;22:353-359.

Li X, Yu X, Zhou D, et al. CCT020312 inhibits triple-negative breast cancer through PERK pathway-mediated G1 phase cell cycle arrest and apoptosis. Front Pharmacol. 2020;11:737 (12 pages).

Ljungberg B, Bensalah K, Canfield St, et al. EAU guidelines on renal cell carcinoma: 2014 update. Eur Urol. 2015;67:913-924.

Low G, Huang G, Fu W, et al. Review of renal cell carcinoma and its common subtypes in radiology. World J Radiol. 2016;8:484-500.

Makhov P, Naito S, Haifler M. The convergent roles of NF-κB and ER stress in sunitinib-mediated expression of pro-tumorigenic cytokines and refractory phenotype in renal cell carcinoma. Cell Death Dis. 2018;9(374) (9 pages).

Martín-Pérez R, Palacios C, Yerbes R, et al. Activated ERBB2/HER2 licenses sensitivity to apoptosis upon endoplasmic reticulum stress through a PERK-dependent pathway. Cancer Res. 2014;74(6):1766-1777.

Moch H, Cubilla AL, Humphrey PA, et al. The 2016 WHO Classification of Tumours of the Urinary System and Male Genital Organs-Part A: Renal, Penile, and Testicular Tumours. Eur Urol. 2016; 70(1):93-105.

Mollica V, Di Nunno V, Massari F. Pembrolizumab plus axitinib: a new treatment option for patients with metastatic renal cell carcinoma. *Chin Clin Oncol* 2019;8:S21. (4 pages).

Motzer RJ, Hutson TE, Tomczak P, et al. Sunitinib versus interferon alpha in metastatic renal-cell carcinoma. N Engl J Med. 2007;356:115-24.

Motzer RJ, Jonasch E, Agarwal N, et al. Kidney Cancer, Version 2.2017, NCCN Clinical Practice Guidelines in Oncology. J Natl Compr Canc Netw. 2017;15(6):804-834.

Motzer RJ, Jonasch E, Agarwal N, et al. Kidney cancer, version 3.2015. J Natl Compr Canc Netw. 2015;13:151-159.

Motzer RJ, Jonasch E, Boyle S, et al. Kidney Cancer, Version 1.2021 Featured Updates to the NCCN Guidelines. J Natl Compr Can Netw. 2020;18:1160-1170.

Motzer RJ, Jonasch E, Michaelson MD, et al. NCCN Guidelines Insights: Kidney Cancer, Version 2.2020. J Natl Compr Canc Netw. 2019; 17(11): 1278-1285.

Nabi S, Kessler E, Bernard B, et al. Renal cell carcinoma: a review of biology and pathophysiology. F1000 Res. 2018;7:307.

Novoa I, Zhang Y, Zeng H, et al. Stress-induced gene expression requires programmed recovery from translational repression. EMBO J. 2003;22(5):1180-1187.

Ojha R, Amaravadi RK. Targeting the unfolded protein response in cancer. Pharmacol Res. 2017;120:258-266. (21 pages).

Ozcan U, Ozcan L, Yilmaz E, et al. Loss of the tuberous sclerosis complex tumor suppressors triggers the unfolded protein response to regulate insulin signaling and apoptosis. Mol Cell. 2008;29(5):541-551.

Pommier A, Anaparthy N, Memos N, Kelley ZL, Gouronnec A, Yan R, Auffray C, Albregues J, Egeblad M, Iacobuzio-Doonahue CA, Lyons SK, Feron DT. Unresolved endoplasmic reticulum stress engenders immune-resistant, latent pancreatic cancer metastases. Science. 2018;360(6394). (26 pages).

Rajasekhar VK, Holland EC. Postgenomic global analysis of translational control induced by oncogenic signaling. Oncogene. 2004;23(18):3248-3264.

(56) References Cited

OTHER PUBLICATIONS

Rajasekhar VK, Viale A, Socci ND, et al. Oncogenic Ras and Akt signaling contribute to glioblastoma formation by differential recruitment of existing mRNAs to polysomes. Mol Cell. 2003;12(4):889-901.
Ranganathan AC, Ojha S, Kourtidis A, Conklin DS, Aguirre-Ghiso JA. Dual function of pancreatic endoplasmic reticulum kinase in tumor cell growth arrest andsurvival. Cancer Res 2008; 68:3260-3268.
Rodler S, Schott M, Tamalunas A, et al. Safety and Efficacy of Robotic Radiosurgery for Visceral and Lymph Node Metastases of Renal Cell Carcinoma: A Retrospective, Single Center Analysis. Cancers (Basel). 2021;13:680. (9 pages).
Rojo F, Najera L, Lirola J, etc. 4E-binding protein 1, a cell signaling hallmark in breast cancer that correlates with pathologic grade and prognosis. Clin Cancer Res. 2007;13(1):81-89.
Romero-Ramirez L, Cao H, Regalado MP, et al. X box-binding protein 1 regulates angiogenesis in human pancreatic adenocarcinomas. Transl Oncol. 2009;2(1):31-38.
Rouschop KM, Dubois LJ, Keulers TG, et al. PERK/eIF2α signaling protects therapy resistant hypoxic cells through induction of glutathione synthesis and protection against ROS. Proc Natl Acad Sci USA. 2013;110(12):4622-4627.
Rouschop KM, Van Den Beucken T, Dubois L, et al. The unfolded protein response protects human tumor cells during hypoxia through regulateon of the autophagy genes MAP1LC3B and ATG5. J Clin Invest. 2010;120(1):127-141.
Sanchez-Gastaldo A, Kempf E, Gonzalez del Alba A, Duran I. Systemic treatment of renal cell cancer: A comprehensive review. Cancer Treat Rev. 2017;60:77-89.
Schewe DM, Aguirre-Ghiso JA. ATF6α-Rheb-mTOR signaling promotes survival of dormant tumor cells in vivo. Proc Nat Acad Sci USA. 2008; 105(30):10519-10524.
Sepe P, Mennitto A, Corti F, Procopio G. Immunotherapeutic Targets and Therapy for Renal Cell Carcinoma. Immunotargets Ther. 2020;9:273-288.
Sequeira SJ, Wen HC, Avivar-Valderas A, et al. Inhibition of eIF2α dephosphorylation inhibits ErbB2-induced deregulation of mammary acinar morphogenesis. BMC Cell Biol. 2009;10(1):64.
Siegel RL, Miller KD, Jemal A. Ca Cancer J Clin. 2020;70(1):7-30.
Siva S, Kothari G, Muacevic A, et al. Radiotherapy for renal cell carcinoma: renaissance of an overlooked approach. Nat Rev Urol. 2017;14(9):549-563.
Sternberg CN, Davis ID, Mardiak J, et al. Pazopanib in locally advanced or metastatic renal cell carcinoma: results of a randomized phase III trial. J Clin Oncol. 2010;28:1061-1068.
Surveillance, Epidemiology, and End Results (SEER) Program. Cancer Stat Facts: Kidney and Renal Pelvis Cancer. Available at: https://seer.cancer.gov/statfacts/html/kidrp.html.
Tacconi EMC, Tuthill M, Protheroe A. Review of Adjuvant Therapies in Renal Cell Carcinoma: Evidence to Date. Onco Targets Ther. 2020;13:12301-12316.
Tameire F, Verginadis II, Koumenis C. Cell intrinsic and extrinsic activators of the unfolded protein response in cancer: mechanisms and targets for therapy. Semin Cancer Biol. 2015;33:3-15.
Urra H, Dufey E, Avril T, et al. Endoplasmic reticulum stress and the hallmarks of cancer. Trend Cancer. 2016;2(5):252-262.
Vijayaraghavan S, Karakas C, Doostan I, et al. CDK4/6 and autophagy inhibitors synergistically induce senescence in Rb positive cytoplasmic cyclin E negative cancers. Nat Commun. 2017;8(1):1-7.
Walczak A, Gradzik K, Kabzinski J, et al. The Role of the ER-Induced UPR Pathway and the Efficacy of Its Inhibitors and Inducers in the Inhibition of Tumor Progression. Oxid Med Cell Longev. 2019;5729710. (15 pages).
Walter P, Ron D. The unfolded protein response: from stress pathway to homeostatic regulation. Science. 2011;334(6059):1081-1086.
Wang L, Cai W, Kong W, et al. Plasma fibrinogen as prognostic predictor in patients with metastatic renal cell carcinoma receiving target therapy. Transl Cancer Res 2018;7:1384-1392.
Wang X, Zhang H, Chen X. Drug resistance and combating drug resistance in cancer. Cancer Drug Resist. 2019;2:141-160.
Weir HK, Thompson TD, Soman A, et al. The Past, Present, and Future of Cancer Incidence in the United States: 1975 Through 2020. Cancer. 2015;121(11):1827-1837.
Yang DC, Chen CH. Potential New Therapeutic Approaches for Renal Cell Carcinoma. Semin Nephrol. 2020;40:86-97.
Ye J, Kumanova M, Hart LS, et al. The GCN2-ATF4 pathway is critical for tumour cell survival and proliferation in response to nutrient deprivation. EMBO J. 2010;29(12):2082-2096.
Yoo YS, Han HG, Jeon YJ. Unfolded Protein Response of the Endoplasmic Reticulum in Tumor Progression and Immunogenicity. Oxid Med Cell Longev. 2017;2969271. (18 pages).
Zhang S, Zhang E, Long J, et al. Immune infiltration in renal cell carcinoma. Cancer Sci. 2019;110(5):1564-1572.
Nagelkerke et al. "Hypoxia stimulates migration of breast cancer cells via the PERK/ATF4/LAMP3-arm of the unfolded protein response" Breast Cancer Research 2013, 15:R2; 1-13.
Jeffrey M. Axten et al.: "Discovery of 7-Methyl-5-(1-{[3-(trifluoromethyl)phenyl]acetyl}-2,3-dihydro-1H-indol-5-yl)-7H-pyrrolo92,3-d]pyrimidin-4-amine (GSK2606414), a Potent and Selective First-in-Class Inhibitor of Protein Kinase R (PKR)-like Endoplasmic Reticulum Kinase (PERK)", Journal of Medicinal Chemistry, vol. 55, No. 16, Aug. 23, 2012, pp. 7193-7207.
Jeffrey M. Axten et al.: "Discovery of GSK2656157: An Optimized PERK Inhibitor Selected for Preclinical Development", ACS Medicinal Chemistry Letters, vol. 4, No. 10, Aug. 23, 2013, pp. 964-968.
Jeffrey M. Axten: "Protein kinase R (PKR)-like endoplasmic reticulum kinase (PERK) inhibitors: a patent review (2010-2015)", Expert Opinion on Therapeutic Patentes, vol. 27, No. 1, Jan. 2, 2017, pp. 37-48.
Sujata Chakraborty et al.: "Targeting Dynamic ATP-Binding Site Features Allows Discrimination between Highly Homologous Protein Kinases", ACS Chemical Biology, vol. 14, No. 6, Apr. 30, 2019, 1249-1259 (19 pages).
Chapman E. et al: "A small molecule inhibitor selective for a variant ATP-binding site of the chaperonin Gro-EL", Bioorganic & Medicinal Chemistry Letters, vol. 19, No. 3, Feb. 1, 2009, pp. 811-813 (7 pages).
Li Chuansheng et al.: "Discovery of novel anti-angiogenesis agents. Part 7: Multitarget inhibitors of VEGFR-2 TIE-2 and EphB4", European Journal of Medicinal Chemistry, vol. 141, Oct. 12, 2017, 506-518.
Bibha Dahal et al.: "PERK is Critical for Alphavirus Nonstructural Protein Translation", Viruses, vol. 13, No. 5, May 12, 2021, 892 (17 pages).
Ryo Kunimoto et al: "Combining Similarity Searching and Network Analysis for the Identification of Active Compounds", ACS Omega, vol. 3, No. 4, Apr. 3, 2018, 3768-3777.
Yan Li et al: "AutoT&T v.2: An Efficient and Versatile Tool for Lead Structure Generation and Optimization", Journal of Chemical Information and Modeling, vol. 56, No. 2, Feb. 22, 2016, 435-453.
Yueshan Li et al: "Identification of5-(2,3-Dihydro-1H-indol-5-yl)-7H-pyrrolo[2,3-d]pyrimidin-4-amine Derivatives as a New Class of Receptor-Interacting Protein Kinase 1 (RIPK1) Inhibitors, Which Showed Potent Activity in a Tumor Metastasis Model", Journal of Medicinal Chemistry, vol. 61, No. 24, Nov. 27, 2018, 11398-11414.
Lydia P. Liew et al: "Hypoxia-Activated Prodrugs of PERK Inhibitors", Chemistry—An Asian Journal, vol. 14, No. 8, Jan. 29, 2019, pp. 1238-1248.
Adrian L. Smith et al.: "Discovery of 1 H-Pyrazolo-3(2H)-ones as Potent and Selective Inhibitors of Protein Kinase R-like Endoplasmic Reticulum Kinase (PERK)", Journal of Medicinal Chemistry, vol. 58, No. 3, Feb. 12, 2015, pp. 1426-1441.
Xue Yuan et al: "Identification of Pyrrolo[2,3-d]pyrimidine-Based Derivatives as Potent and Orally Effective Fms-like Tyrosine Receptor Kinase 3 (FLT3) Inhibitors for Treating Acute Myelogenous leukemia", Journal of Medicinal Chemistry, vol. 62, No. 8, Apr. 2, 2019, 4158-4173.

(56) References Cited

OTHER PUBLICATIONS

Sandoval et al., "Inhibition as a possible therapy for hypoxia-induced solidary dormant tumor cells" Abstract A45, Proceedings of the AACR Special Conference on Tumor Metastasis, vol. 76, No. 7, Nov. 30, 2015 (3 pages).
Sosa et al., "Mechanisms of disseminated cancer cell dormancy: an awakening field" Nature Reviews. Cancer, vol. 14, No. 9, Aug. 14, 2014, pp. 611-622 (27 pages).
Shan Yuanyuan et al: "Expanding the structural diversity of diarylureas as multi-target tyrosine kinase inhibitors", Bioorganic & Medicinal Chemistry, vol. 24, No. 4, Dec. 23, 2015, pp. 750-758.
Aguirre-Ghiso et al: "Targeting dormant cancer", Nature Medicine, vol. 19, No. 3, Mar. 6, 2013, pp. 276-277 (4 pages).

PHENYL-2-HYDROXY-ACETYLAMINO-2-METHYL-PHENYL COMPOUNDS FOR THE TREATMENT OF PANCREATIC CANCER

CROSS-REFERENCE TO RELATED APPLICATIONS

This application is a U.S. National Phase Application of PCT/US2018/027005, filed on Apr. 11, 2018, which claims priority and benefit of European Patent Application No. 17382207.3, filed Apr. 18, 2017, contents of which are each incorporated by reference in their entirety.

BACKGROUND OF THE INVENTION

The present invention relates to novel phenyl-2-hydroxy-acetylamino-2-methyl-phenyl compounds, to pharmaceutical compositions comprising the compounds, to methods of using the compounds to treat physiological disorders, and to intermediates and processes useful in the synthesis of the compounds.

The present invention is in the field of treatment of cancer and, other diseases and disorders involving protein kinase R (PKR)-like endoplasmic reticulum kinase (PERK). PERK, an eIF2 kinase involved in the unfolded protein response (UPR) regulates protein synthesis, aids cells to alleviate the impact of endoplasmic reticulum stress and has been implicated in tumor genesis and cancer cell survival.

Tumor cells thrive in a hostile microenvironment caused mainly by nutrient and oxygen limitation, high metabolic demand, and oxidative stress. These stresses are known to disrupt the protein folding capacity of the endoplasmic reticulum (ER) eliciting a cellular remediation response known as the unfolded protein response (UPR). ER stress contributes to greater tumorigenic potential of cancer cells, tumor metastasis, tumor drug resistance, and the ability of cancer cells to avoid effective immune responses.

There are three major ER transmembrane sensors of the UPR: 1) inositol requiring enzyme (IRE1α/IRE1β, encoded by ERN1 and ERN2, respectively); 2) PKR-like ER kinase (PERK, also known as PEK, encoded by EIF2AK3); and 3) the activating transcription factor 6α (encoded by ATF6). Each of these three sensors is regulated similarly through binding of the ER luminal chaperone protein GRP78 or BiP (encoded by HSPA5). When protein folding demands of the ER exceed capacity, reduced BiP binding results in activation of these ER sensor proteins resulting in the induction of coordinated signaling pathways to increase the folding capacity of the ER and alleviate the underlying stress. Effective responses lead to cell adaptation and survival while irreparable ER stress triggers cell death and apoptosis.

PERK is a type I transmembrane serine/threonine kinase and a member of a family of kinases that phosphorylate the eukaryotic translation initiation factor 2α (eIF2-α) and regulate translation initiation. Other family members include HRI (EIF2AK1), PKR (EIF2AK2), and GCN2 (EIF2AK4). Each eIF2 kinase responds to different cellular stress signals to regulate general translation and gene specific translational control. Phosphorylation of eIF2 results in reduced initiation of general translation due to a reduction in eIF2B exchange factor activity decreasing the amount of protein entering the ER (and thus the protein folding burden) and translational demand for ATP. Phosphorylation of eIF2 also increases translation of some mRNAs in a gene specific manner including the transcription factor ATF4. ATF4 transcriptional targets include numerous genes involved in cell adaptation and survival including several involved in protein folding, nutrient uptake, amino acid metabolism, redox homeostasis, and autophagy (4). Selective inhibition of the PERK arm of the UPR is expected to profoundly affect tumor cell growth and survival. As such, compounds which inhibit PERK are believed to be useful in treating cancer.

With the current state of medical treatment, patients developing pancreatic cancer often have a poor prognosis even if the disease is detected early. As such, there remains a significant need for new and effective therapies to treat pancreatic cancer. The compounds of the present invention are inhibitors of PERK, and are believed to be useful in treating cancer, particularly pancreatic cancer.

WO 2015/136463 discloses certain pyrrolidinone derivatives which possess PERK inhibitory activity, and further discloses the compounds as useful in treating cancer and diseases associated with activated unfolded protein response including pancreatic cancer.

DETAILED DESCRIPTION OF THE INVENTION

Accordingly, the present invention provides a compound of formula I:

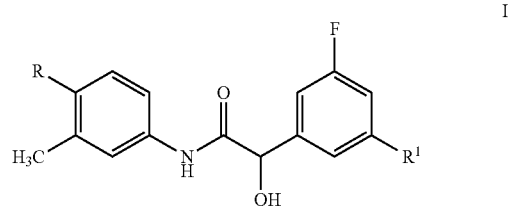

wherein
R is selected from the group consisting of

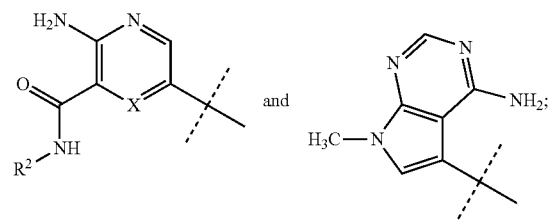

X is CH or N;
R$^1$ is hydrogen or fluoro; and
R$^2$ is C$_1$ to C$_3$ alkyl;
or a pharmaceutically acceptable salt thereof.

In addition, the present invention provides a compound of formula Ia:

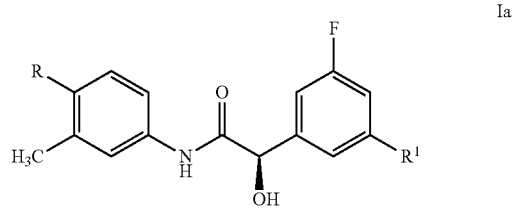

wherein
R is selected from the group consisting of

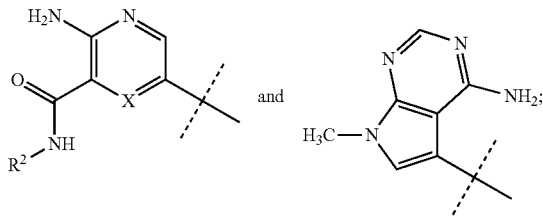

X is CH or N;
R$^1$ is hydrogen or fluoro; and
R$^2$ is C$_1$ to C$_3$ alkyl;
or a pharmaceutically acceptable salt thereof.

In addition, the present invention provides a compound of formula I or Ia:
wherein R is

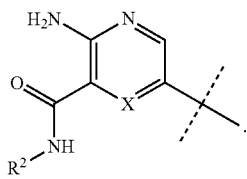

In addition, the present invention provides a compound of formula I or Ia: wherein X is CH or N; R$^1$ is hydrogen or fluoro; and R$^2$ is methyl or isopropyl; or a pharmaceutically acceptable salt thereof.

In addition, the present invention provides a compound of formula I or Ia: wherein R is

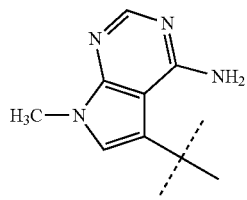

or a pharmaceutically acceptable salt thereof.

In addition, the present invention provides the compound 3-amino-6-[4-[[(2R)-2-(3,5-difluorophenyl)-2-hydroxy-acetyl]amino]-2-methyl-phenyl]-N-methyl-pyrazine-2-carboxamide which may be represented by the formula

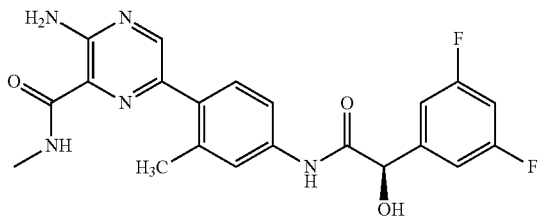 [SMILES: CNC(=O)c1nc(-c2ccc(NC(=O)[C@H](O)c3cc(F)cc(F)c3)cc2C)cnc1N]

or a pharmaceutically acceptable salt thereof.

In addition, the present invention provides the compound 2-amino-5-[4-[[(2R)-2-(3,5-difluorophenyl)-2-hydroxy-acetyl]amino]-2-methyl-phenyl]-N-isopropyl-pyridine-3-carboxamide which may be represented by the formula

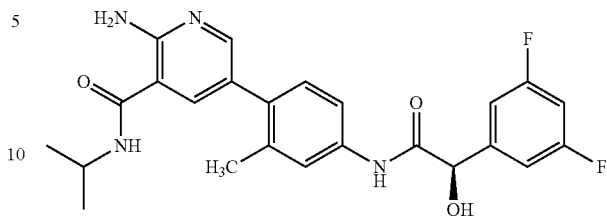

or a pharmaceutically acceptable salt thereof.

In addition, the present invention provides the compound (2R)—N-[4-(4-amino-7-methyl-pyrrolo[2,3-d]pyrimidin-5-yl)-3-methyl-phenyl]-2-(3-fluorophenyl)-2-hydroxy-acetamide which may be represented by the formula

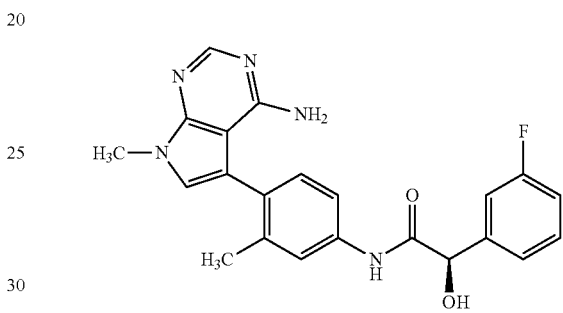

or a pharmaceutically acceptable salt thereof.

The present invention provides a method of treating cancer in a patient in need of such treatment, comprising administering to the patient an effective amount of a compound of formula I or Ia, or a pharmaceutically acceptable salt thereof. The present invention also provides a method of inhibiting PERK activity resulting in antitumor activity in a patient in need of such treatment, comprising administering to the patient an effective amount of a compound of formula I or Ia, or a pharmaceutically acceptable salt thereof.

The present invention also provides a method of treating pancreatic cancer in a patient in need of such treatment, comprising administering to the patient an effective amount of a compound of formula I or Ia, or a pharmaceutically acceptable salt thereof.

In addition, the present invention provides a compound of formula I or Ia, or pharmaceutically acceptable salt thereof for use in therapy, in particular for the treatment of pancreatic cancer. Further, the present invention provides a compound of formula I or Ia, or pharmaceutically acceptable salt thereof for use in the treatment of pancreatic cancer. In a further embodiment, the present invention provides the use of a compound of the invention, or a pharmaceutically acceptable salt thereof, for the manufacture of a medicament for the treatment of pancreatic cancer.

The invention further provides a pharmaceutical composition, comprising a compound of the invention, or a pharmaceutically acceptable salt thereof, with one or more pharmaceutically acceptable carriers, diluents, or excipients. In a further embodiment, the composition further comprises one or more other therapeutic agents. The invention further provides a process for preparing a pharmaceutical composition, comprising admixing a compound of formula I or Ia, or a pharmaceutically acceptable salt thereof, with one or more pharmaceutically acceptable carriers, diluents, or excipients. This invention also encompasses novel intermediates and processes for the synthesis of the compounds of formula I and Ia.

As used herein, the terms "treating" or "to treat" includes restraining, slowing, stopping, or reversing the progression or severity of an existing symptom or disorder.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by one skilled in the art by the use of known techniques and by observing results obtained under analogous circumstances. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.1 to about 50 mg/kg of body weight. In some instances, dosage levels below the lower limit of the aforesaid range may be more than adequate, while in other cases still larger doses may be employed with acceptable side effects, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The compounds of the present invention are preferably formulated as pharmaceutical compositions administered by any route which makes the compound bioavailable, including oral, intravenous and transdermal routes. Most preferably, such compositions are for oral administration. Such pharmaceutical compositions and processes for preparing same are well known in the art (See, e.g., *Remington: The Science and Practice of Pharmacy*, L. V. Allen, Editor, 22$^{nd}$ Edition, Pharmaceutical Press, 2012).

It is understood that compounds of formula I may exist as stereoisomers. Embodiments of the present invention include all enantiomers, diastereomers and mixtures thereof. A particular enantiomer of a compound of formula I is represented by a compound of formula Ia

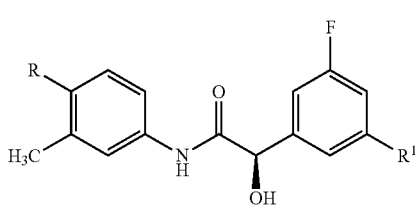

wherein R and $R^1$ are as previously defined.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994. Single enantiomers of compounds of the invention are a preferred embodiment of the invention.

A pharmaceutically acceptable salt of the compounds of the invention can be formed, for example, by reaction of an appropriate free base of a compound of the invention and an appropriate pharmaceutically acceptable acid in a suitable solvent under standard conditions well known in the art. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

In Vitro Inhibition of PERK Enzyme Activity
(Isolated)

Recombinant human EIF2AK2 (PKR) catalytic domain (amino acids 252-551), EIF2AK3 (PERK) catalytic domain (amino acids 536-1116), GFP-eIF2α substrate, and Terbium-labelled phospho-eIF2α antibody is obtained (Invitrogen, Carlsbad, Calif.). Express and purify HIS-SUMO-GCN2 catalytic domain (amino acids 584-1019) from *E. coli*. Perform TR-FRET kinase assays in the absence or presence of inhibitors in a reaction buffer consisting of 50 mM HEPES, pH 7.5, 10 mM $MgCl_2$, 1.0 mM EGTA, and 0.01% Brij-35, and 100-200 nM GFP-eIF2α substrate. PKR assays contain 14 ng/mL enzyme and 2.5 μM ATP ($Km_{,app}$~2.5 μM), PERK assays contain 62.5 ng/mL enzyme and 1.5 μM ATP ($Km_{,app}$~1.5 uM), and GCN2 assays contain 3 nM enzyme and 90 μM ATP ($Km_{,app}$~200 uM). Add test compound, initiate the reaction by addition of enzyme, and incubate at room temperature for 45 minutes. Stop the reaction by addition of EDTA to a final concentration of 10 mM, add Terbium-labelled phospho-eIF2α antibody at a final concentration of 2 nM, and incubate for 90 minutes. Monitor the resulting fluorescence in an EnVison® Multi-label reader (PerkinElmer, Waltham, Mass.). Determine TR-FRET ratios and the resulting $IC_{50}$ values using a 4-parameter nonlinear logistic equation as shown: $Y=(A+4B-A)/(1+((C/x)^D))))$ where, Y=% specific inhibition, A=Bottom of the curve, B=Top of the curve, C=absolute $IC_{50}$ (concentration causing 50% inhibition), and D=hill slope.

The compounds of Examples 1, 5 and 9 were tested essentially as described above and exhibited $IC_{50}$ values shown in Table 1. These data demonstrate that the compounds of Examples 1, 5 and 9 inhibit isolated PERK enzyme activity in vitro.

TABLE 1

| Example No. | Enzyme IC$_{50}$ (µM) | | |
|---|---|---|---|
| | PERK | GCN2 | PKR |
| Example 1 | 0.0022 ± 0.0012 (N = 3) | 18.1 ± 1.5 (N = 2) | >20 (N = 1) |
| Example 5 | 0.0020 ± 0.0005 (N = 3) | 10.8 ± 2.1 (N = 4) | >20 (N = 1) |
| Example 9 | 0.0024 ± 0.0010 (N = 4) | 16.4 ± 2.9 (N = 4) | Not determined |

In Vitro Inhibition of PERK Enzyme Activity
(Whole Cell)

Seed GripTite™ 293 cells (Invitrogen, Carlsbad, Calif.) expressing GFP-eIF2α at 10,000 cells per well in 384-well plates and allow to attach overnight. Pre-treat cells with test compounds for 1 hour. Add Tunicamycin (1 µM) to induce PERK activity and incubate the plates at 37° C. for 2 hours. Remove the culture media and lyse the cells in buffer consisting of 20 mM Tris-HCl, pH 7.5, 150 mM NaCl, 5 mM EDTA, 1% NP-40, 5 mM NaF, Protease inhibitors (Sigma, St. Louis, Mo.), Phosphatase inhibitors (Sigma, St. Louis, Mo.), and 2 nM Terbium-labelled anti-phospho-eIF2 antibody (Invitrogen, Carlsbad, Calif.). Incubate the cell lysates for 2 hours in the dark at room temperature and monitor fluorescence in an EnVison® Multilabel reader (PerkinElmer, Waltham, Mass.). Determine TR-FRET ratios and the resulting IC$_{50}$ values from the fitted inhibition curves using un-induced (100% inhibition) and induced (0% inhibition) wells as controls.

The compounds of Examples 1, 5 and 9 were tested essentially as described above and exhibited IC$_{50}$ values shown in Table 2. These data demonstrate that the compounds of Examples 1, 5 and 9 inhibit whole cell PERK enzyme activity in vitro.

TABLE 2

| Example No. | Cell IC$_{50}$ (µM) |
|---|---|
| Example 1 | 0.054 ± 0.060 (N = 9) |
| Example 5 | 0.117 ± 0.102 (N = 14) |
| Example 9 | 0.028 ± 0.011 (N = 12) |

In Vivo Inhibition of Pancreatic Cancer (Mouse Xenograft Model)

Implant female athymic nude mice (Harlan Laboratories) subcutaneously with 5×10$^6$ BxPC-3 cells containing matrigel on the right flank and monitor tumor growth with calipers. Initiate compound dosing when tumors reach ~250 mm$^3$ and dose mice twice per day by oral gavage (8 animals per group) for 28 days. Formulate compounds in 10% Acacia containing 0.05% anti-foam or 20% Captisol in 25 mM NaPO$_4$ buffer pH 2 for 30 the compounds of Examples 5 and 9, respectively. Treat control animals with Acacia vehicle alone. Estimate tumor volumes using the formula l×w$^2$×(π/6), where l is the larger measured diameter and w is the smaller perpendicular diameter. Calculate percent delta T/C using the formula 100×[(T−T$_0$)/(C−C$_0$)] and percent regression using the formula 100×[(T−T$_0$)/T$_0$], where T and C are mean tumor volumes in the treated and control groups, respectively. T$_0$ and C$_0$ are the corresponding baseline mean tumor volumes. Convert percent delta T/C to percent delta tumor growth inhibition (TGI) using the equation, 100−percent delta T/C. For statistical analysis, transform tumor volume data to log$_{10}$ scale to equalize variance across time and treatment groups. Analyze the log$_{10}$ volume data with a two-way repeated measures analysis of variance (Spatial Power correlation model) by time and treatment using the MIXED procedures in the SAS software package (Version 9.3). Compare treated groups to the control group at each time point.

The compounds of Example 5 and 9 were tested essentially as described above and exhibited tumor growth inhibition values shown in Table 3 and 4 respectively. These data demonstrate that the compounds of Example 5 and 9 inhibit pancreatic tumor growth in vivo.

TABLE 3

Tumor Volume Summary

| | Vehicle Control | | Example 5 30 mg/kg PO BID | | | | |
|---|---|---|---|---|---|---|---|
| Day Post-Implant | Mean (mm$^3$) | SE$^a$ | Mean (mm$^3$) | SE$^a$ | p-value | T/C$^b$ (%) | TGI$^c$ (%) |
| 21 | 108.3 | 4.6 | 123.9 | 13.3 | NA | NA | NA |
| 24 | 115.8 | 7.9 | 132.8 | 11.6 | NA | NA | NA |
| 32 | 153.4 | 13.5 | 143.4 | 10.4 | NA | NA | NA |
| 35 | 163.9 | 10.7 | 174.6 | 17.2 | NA | NA | NA |
| 39 | 180.5 | 13.4 | 183.8 | 19.0 | NA | NA | NA |
| 47 | 206.4 | 19.2 | 213.7 | 20.7 | NA | NA | NA |
| 52$^d$ | 252.2 | 39.6 | 252.0 | 21.6 | NA | NA | NA |
| 60 | 337.0 | 52.9 | 311.8 | 26.7 | 0.667 | 71.5 | 28.5 |
| 67 | 498.1 | 78.2 | 387.8 | 33.2 | 0.182 | 55.8 | 44.2 |
| 72 | 602.3 | 94.6 | 435.0 | 37.3 | 0.084 | 52.7 | 47.3 |
| 74 | 720.0 | 113.0 | 487.5 | 41.8 | 0.039* | 50.7 | 49.3 |
| 76 | 762.5 | 119.7 | 528.8 | 45.3 | 0.052 | 54.5 | 45.5 |
| 79 | 971.5 | 152.5 | 593.2 | 50.8 | 0.010* | 47.7 | 52.3 |

$^a$Standard error of the geometric mean tumor volume
$^b$Calculated using 100 × [(T−T$_0$)/(C−C$_0$)], where T and C are mean tumor volumes in the treated and control groups, respectively; T$_0$ and C$_0$ are the corresponding baseline mean tumor volumes.
$^c$TCI is Tumor Growth Inhibition, calculated using 100−% T/C
$^d$Day of randomization and start of treatment
*Significant, p < 0.05

TABLE 4

Tumor Volume Summary

| | Vehicle Control | | Example 9 30 mg/kg PO BID | | | | |
|---|---|---|---|---|---|---|---|
| Day Post-Implant | Mean (mm$^3$) | SE$^a$ | Mean (mm$^3$) | SE$^a$ | p-value | T/C$^b$ (%) | TGI$^c$ (%) |
| 21 | 108.3 | 4.6 | 111.9 | 7.5 | NA | NA | NA |
| 24 | 115.8 | 7.9 | 134.3 | 8.4 | NA | NA | NA |
| 32 | 153.4 | 13.5 | 153.7 | 12.4 | NA | NA | NA |
| 35 | 163.9 | 10.7 | 162.6 | 14.6 | NA | NA | NA |
| 39 | 180.5 | 13.4 | 167.1 | 12.8 | NA | NA | NA |
| 47 | 206.4 | 19.2 | 196.4 | 15.5 | NA | NA | NA |
| 52$^d$ | 252.2 | 39.6 | 244.2 | 28.4 | NA | NA | NA |
| 60 | 337.0 | 52.9 | 284.8 | 33.2 | 0.367 | 40.8 | 59.2 |
| 67 | 498.1 | 78.2 | 317.2 | 36.9 | 0.018* | 27.4 | 72.6 |
| 72 | 602.3 | 94.6 | 380.5 | 44.3 | 0.016* | 37.3 | 62.7 |
| 74 | 720.0 | 113.0 | 418.3 | 48.7 | 0.005* | 36.0 | 64.0 |

TABLE 4-continued

Tumor Volume Summary

| Day | Vehicle Control | | Example 9 30 mg/kg PO BID | | | | |
|---|---|---|---|---|---|---|---|
| Post-Implant | Mean (mm$^3$) | SE[a] | Mean (mm$^3$) | SE[a] | p-value | T/C[b] (%) | TGI[c] (%) |
| 76 | 762.5 | 119.7 | 480.4 | 55.9 | 0.015* | 45.1 | 54.9 |
| 79 | 971.5 | 152.5 | 541.6 | 63.1 | 0.002* | 40.5 | 59.5 |

[a]Standard error of the geometric mean tumor volume
[b]Calculated using 100 × [(T-T$_0$)/(C-C$_0$)], where T and C are mean tumor volumes in the treated and control groups, respectively, T$_0$ and C$_0$ are the corresponding baseline mean tumor volumes.
[c]TCI is Tumor Growth Inhibition, calculated using 100-% T/C
[d]Day of randomization and start of treatment
*Significant, p < 0.05

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention. In addition, one of ordinary skill in the art appreciates that the compounds of formula Ia may be prepared by using starting material with the corresponding stereochemical configuration which can be prepared by one of skill in the art. For example, the Schemes below utilize starting materials with the configuration corresponding ultimately to formula Ia.

Generally, a compound of formula I may be prepared from a compound of formula III (Scheme 1). More specifically, a compound of formula III is reacted with a compound of formula II and a suitable coupling reagent such as HATU (1-[bis(dimethylamino)methylene]-1H-1,2,3-triazolo[4,5-b]pyridinium 3-oxid hexafluorophosphate) in the presence of a suitable amine base such as N,N-diisopropylethylamine or trimethylamine. A compound of formula I may be separated into its isomers by chiral chromatography.

Correspondingly, compound of formula Ia may be prepared from the compound of formula IIa. More specifically, a compound of formula III is reacted with a compound of formula IIa and a suitable coupling reagent such as HATU (1-[bis(dimethylamino)methylene]-1H-1,2,3-triazolo[4,5-b]pyridinium 3-oxid hexafluorophosphate) in the presence of a suitable amine base such as N,N-diisopropylethylamine or trimethylamine. A compound of formula IIa may be prepared from a compound of formula II with a lipolytic enzyme such as Lipase PS Amano SD. Further information regarding this optical resolution technique may be found in Mendiola, J. et al, *Org. Process Res. Dev.* 2012, 16, 1312-1316.

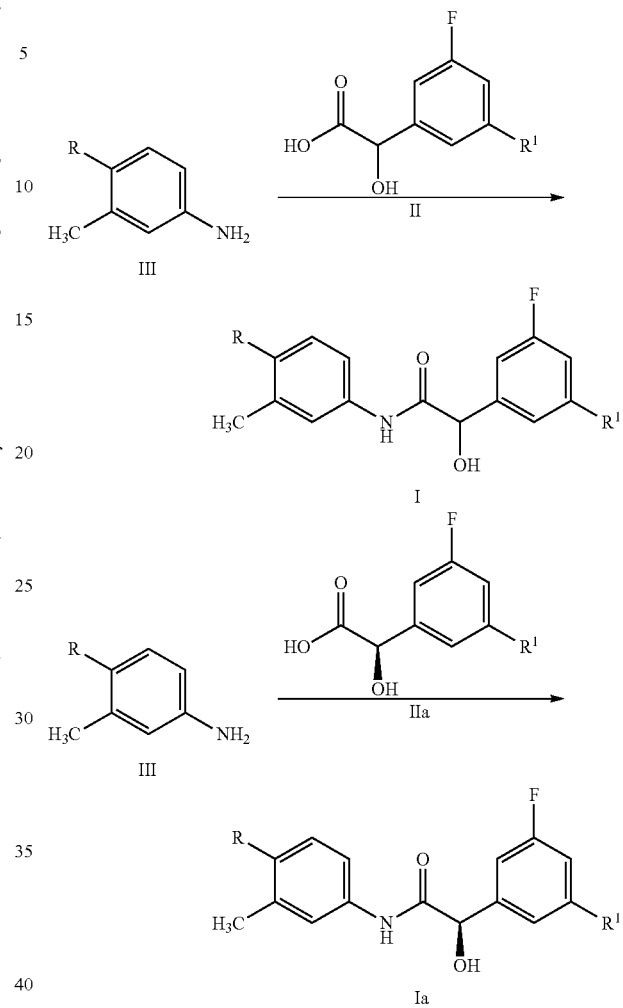

Scheme 1

Generally, a compound of formula III may be prepared from a compound of formula IV. A compound of formula III may be obtained by treating a compound of formula R-Br with 3-methyl-4-(4,4,5,5-tetramethyl-1,3,2-dioxaborolan-2-yl)aniline in the presence of a base such as K$_2$CO$_3$ and a palladium catalyst such as Pd(dppf)$_2$Cl$_2$.

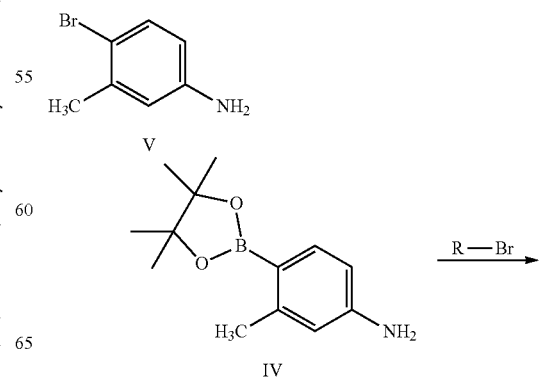

Scheme 2

-continued

R—Br is

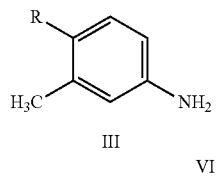
III or

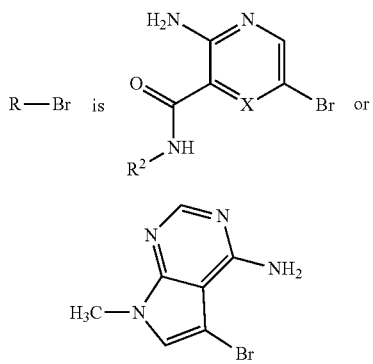
VI

VII

A compound of formula R-Br, represented by a compound of formula VI or VII, may be prepared by procedures known in the chemical arts as well as procedures described in the Preparations and Examples below.

Preparation 1

Synthesis of 4-chloro-7-methyl-pyrrolo[2,3-d]pyrimidine

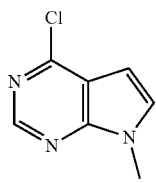

Add $Cs_2CO_3$ (845 g, 2.60 mol) at 15° C. to a solution of 4-chloro-7H-pyrrolo[2,3-d]pyrimidine (200 g, 1.29 mol) in N-methyl-2-pyrrolidone (1.20 L). Warm to 23° C., add MeI (202 g, 1.43 mol) dropwise over 30 min, and stir for 4 h. After this time, pour onto ice-water (2.00 L) and stir for 30 min. Filter, then slurry material in $H_2O$ (1.00 L). Filter and dry to give the title compound (180 g, 81%). ES/MS m/z ($^{35}Cl$) 168.0 (M+H).

Preparation 2

Synthesis of 5-bromo-4-chloro-7-methyl-pyrrolo[2,3-d]pyrimidine

Add N-bromosuccinimide (418 g, 2.35 mol) portionwise over 20 min at 15° C. to a solution of 4-chloro-7-methyl-pyrrolo[2,3-d]pyrimidine (355 g, 2.12 mol) in dichloromethane (3.19 L), and stir at 23° C. for 3 h. After this time, filter, wash with $H_2O$ (5.32 L), and dry to give the title compound (448 g, 86%) as a white solid. ES/MS m/z ($^{35}Cl$, $^{79}Br$) 245.9 (M+H).

Preparation 3

Synthesis of 5-bromo-7-methyl-pyrrolo[2,3-d]pyrimidin-4-amine

Stir a suspension of 5-bromo-4-chloro-7-methyl-pyrrolo[2,3-d]pyrimidine (454 g 1.84 mol) in ammonia (30% in $H_2O$, 3.63 L) at 120° C. in a Hastelloy™ pressure vessel for 18 h. Cool to 20° C., filter, wash with $H_2O$ (1.80 L) and methanol (900 mL), and dry to give the title compound (351 g, 82%) as a white solid. ES/MS m/z ($^{79}Br$) 227.2 (M+H).

Preparation 4

Synthesis of 3-amino-6-bromo-pyrazine-2-carboxylic acid

Add 3-aminopyrazine-2-carboxylic acid (50.0 g, 369.4 mmol) to a solution of N-bromosuccinimide (61.2 g, 377.3 mmol) and dimethylformamide (236.3 g, 3.2 mole) at 0° C. After 1 hour at room temperature, an orange solid is formed. Wash the solid residue with ethyl acetate (500 mL) and discarded it. Dry the organic phase with sodium sulfate, filter, and concentrate under reduced pressure to yield the title compound as a white solid (32.0 g, 146.7 mmol, 41%). ES/MS m/z ($^{79}Br/^{81}Br$) 217.1/219.0 (M+H).

Preparation 5

Synthesis of 3-amino-6-bromo-N-methyl-pyrazine-2-carboxamide

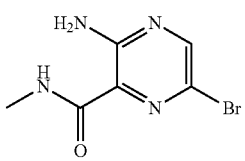

Treat a solution of 3-amino-6-bromo-pyrazine-2-carboxylic acid (214 g, 983 mmol) in dimethylformamide (1.07 L) with methylamine hydrochloride (79.7 g, 1.18 mol) and N,N-diisopropylethylamine (445 g, 3.44 mol) at 23° C. To the resulting suspension, add 1-[bis(dimethylamino)methylene]-1H-1,2,3-triazolo[4,5-b]pyridinium 3-oxid hexafluorophosphate (449 g, 1.18 mol) over 30 min. After 30 min, add $H_2O$ (4.29 L) over 2 h. Stir at 23° C. for 30 min and then 1 h at 10° C. Filter, wash the solid with $H_2O$ (2×428 mL), and dry to give the title compound (227 g, 82%). ES/MS m/z ($^{79}$Br) 231.0 (M+H).

Preparation 6

Synthesis of 2-amino-5-bromo-N-isopropyl-pyridine-3-carboxamide

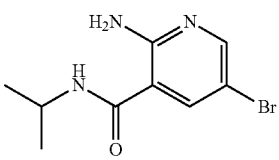

Add propan-2-amine (42.5 g, 0.719 mol), 1-ethyl-3-(3-dimethylaminopropyl)carbodiimide (127 g, 0.664 mol) and hydroxybenzotriazole (89.7 g, 0.660 mol) to a suspension of 2-amino-5-bromo-pyridine-3-carboxylic acid (120 g, 0.553 mol) in tetrahydrofuran (1.2 L) at 12° C. Stir the mixture at 23° C. overnight. Add ethyl acetate (250 mL) and aqueous saturated $NaHCO_3$ (250 mL), separate phases, and extract aqueous layer with ethyl acetate (2×150 mL). Wash combined organic phases with $H_2O$ (300 mL) and saturated aqueous NaCl (300 mL), and concentrate under reduced pressure to give the title compound (125 g, 88%). ES/MS m/z ($^{79}$Br) 258.0 (M+H).

Preparation 7

Isolation of (2R)-2-(3,5-difluorophenyl)-2-hydroxy-acetic acid

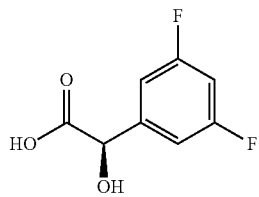 [SMILES: O=C(O)[C@H](O)c1cc(F)cc(F)c1]

Support lipase PS Amano (see Mendiola, J. et al, *Org. Process Res. Dev.* 2012, 16, 1312-1316) in diatomaceous earth prior to use by mixing 200 g of diatomaceous earth and 200 g of lipase PS Amano SD. Add $H_2O$ to cover the solid, and mix the mixture. Remove $H_2O$ in an oven at 4 mbar and 40° C. for 16 h. Check $H_2O$ is below 1% through Karl Fischer titration for water determination.

Add supported lipase PS amano SD (250 g) and vinyl acetate (312 mL; 3.36 mol to a suspension of racemic 2-(3,5-difluorophenyl)-2-hydroxyacetic acid (125 g, 664 mmol) in methyl tert-butyl ether (2.50 L), and stir the mixture at 26° C. for 72 h. After this time, filter, rinse the solid with methyl tert-butyl ether (1.50 L), and concentrate combined filtrates under reduced pressure. Slurry the residue in dichloromethane (160 mL) at 23° C. for 4 h. Filter, wash the solid with petroleum ether (150 mL), and dry to give the title compound (47.0 g, 36%). $^1$H NMR ($d_6$-DMSO) δ 5.11 (s, 1H), 6.20 (bs, 1H), 7.11-7.21 (m, 3H), 12.8 (bs, 1H). Absolute configuration is determined by vibrational circular dichroism (see Freedman T. B et al, *Chirality,* 2003 Nov. 15(9), 743-758). Chiral HPLC: Rt=7.39 min (UV); Column: Chiralpak® AD 4.6×150 mm 5 μm; 5% EtOH in n-hexane (0.05% TFA) isocratic; Flow Rate: 1.5 mL/min, ee>98%.

Preparation 8

Isolation of (2R)-2-(3-fluorophenyl)-2-hydroxy-acetic acid

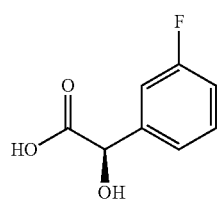 [SMILES: O=C(O)[C@H](O)c1cccc(F)c1]

Support lipase PS Amano SD (see Mendiola, J. et al, *Org. Process Res. Dev.* 2012, 16, 1312-1316) in diatomaceous earth prior to use by mixing 100 g of diatomaceous earth and 100 g of lipase PS Amano SD. Add $H_2O$ to cover the solid, and mix the mixture. Remove $H_2O$ in an oven at 4 mbar and 40° C. for 16 h. Check $H_2O$ is below 1% through Karl Fischer titration for water determination.

Add supported lipase PS amano SD (200 g) and vinyl acetate (269 mL; 2.90 mol to a suspension of racemic 2-(3-fluorophenyl)-2-hydroxyacetic acid (96 g, 560 mmol) in methyl tert-butyl ether (2.00 L), and stir the mixture at 26° C. for 90 h. After this time, filter, rinse the solid with methyl tert-butyl ether (1.50 L), and concentrate combined filtrates under reduced pressure. Slurry the residue in dichloromethane (160 mL) at 23° C. for 4 h. Filter, wash the solid with petroleum ether (150 mL), and dry to give the title compound (31.0 g, 32%). $^1$H NMR ($d_6$-DMSO) δ 5.07 (s, 1H), 6.17 (bs, 1H), 7.12 (m, 1H), 7.23 (m, 1H), 7.39 (m, 1H), 12.8 (bs, 1H). $[α]_D^{20}$=−119° (C=2.83, acetone). Chiral HPLC: Rt=10.22 min (UV); Column: Chiralpak® AD 4.6×150 mm 5 μm; 5% EtOH in n-hexane (0.05% TFA) isocratic; Flow Rate: 1.5 mL/min, ee>98%.

Preparation 9

Synthesis of 3-methyl-4-(4,4,5,5-tetramethyl-1,3,2-dioxaborolan-2-yl)aniline

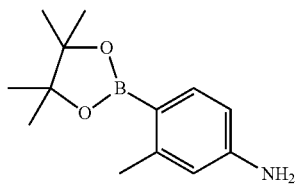 [SMILES: Cc1cc(N)ccc1B1OC(C)(C)C(C)(C)O1]

Heat a suspension of tricyclohexylphosphine (59.85 g, 213 mmol) in 1,4-dioxane (2.98 L) at 95° C. for 10 min, until a solution is obtained. Then, add 4-bromo-3-methylaniline (752 g, 2.67 mol), bis(pinacolato)diboron (745.17 g, 2.93 mol), potassium acetate (524 g, 5.34 mol), and palladium(II) acetate (23.96 g, 107 mmol), and continue heating the mixture at 95° C. for 4 h. After this time, cool to 23° C., dilute with methyl tert-butyl ether (2.5 L), filter through diatomaceous earth, and rinse the solid with methyl tert-butyl ether (1 L). Combine filtrates, wash with $H_2O$ (1.5 L) and saturated aqueous NaCl (1.2 L), and concentrate under reduced pressure to obtain title compound (593 g, 95%). To obtain an analytical sample, slurry with hexane (1.6 mL/g) at 40° C. for 2 h, then cool to 23° C., filter and wash solid with hexane (2×0.5 mL/g). ES/MS m/z 234.1 (M+H).

Preparation 10

Synthesis of 2-Amino-5-(4-amino-2-methyl-phenyl)-N-isopropyl-pyridine-3-carboxamide

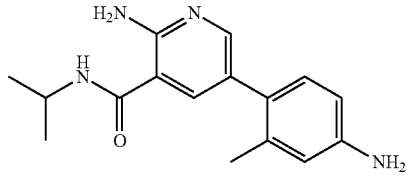 [SMILES: Cc1cc(N)ccc1-c1cnc(N)c(C(=O)NC(C)C)c1]

Add 3-methyl-4-(4,4,5,5-tetramethyl-1,3,2-dioxaborolan-2-yl)aniline (93.6 g, 0.401 mol), $K_2CO_3$ (119 g, 0.860 mol), and Pd(dppf)2Cl$_2$ (10.6 g, 140 mmol) to a solution of 2-amino-5-bromo-N-isopropyl-pyridine-3-carboxamide (74.0 g, 0.287 mol) in dioxane (888 mL) and $H_2O$ (296 mL), and heat the mixture at 55° C. overnight. Cool to 23° C., add ethyl acetate (150 mL), filter the resulting suspension through diatomaceous earth, and rinse solid with ethyl acetate (50 mL). Wash combined filtrates with $H_2O$ (30 mL) and saturated aqueous NaCl (300 mL), and concentrate under reduced pressure to give the title compound (78.0 g, 96%). ES/MS m/z 285.1 (M+H).

Preparation 11

Synthesis of 3-amino-6-(4-amino-2-methylphenyl)-N-methylpyrazine-2-carboxamide

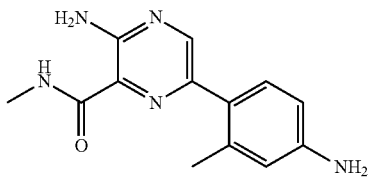

Add 3-amino-6-bromo-N-methylpyrazine-2-carboxamide (99.1 g, 429 mmol), $Na_2CO_3$, (2 M in $H_2O$, 500 mL, 1.00 mol), and 1,1'-bis(diphenylphosphino)ferrocene)palladium (II) chloride (19 g, 22.8 mmol) to a solution of 3-methyl-4-(4,4,5,5-tetramethyl-1,3,2-dioxaborolan-2-yl)aniline (122 g, 450 mmol) in 1,4-dioxane (3.00 L), and heat the mixture to 85° C. for 32 h. Cool to 30° C., add ethyl acetate (4.00 L), filter through a silica gel pad, and rinse the solid with ethyl acetate (3×1.00 L). Wash combined filtrates with $H_2O$ (2×1.50 L), and concentrate under reduced pressure. Purify residue by chromatography (eluent: petroleum ether/ethyl acetate 5:1 to 1:1) to give the title compound (80 g, 72%) as a yellow solid. ES/MS m/z 258.1 (M+H).

Preparation 12

Synthesis of 5-(4-amino-2-methyl-phenyl)-7-methyl-pyrrolo[2,3-d]pyrimidin-4-amine

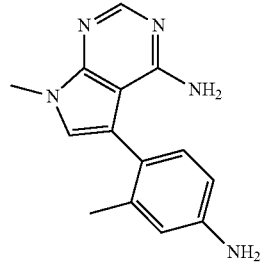 [SMILES: Cc1cc(N)ccc1-c1cn(C)c2ncnc(N)c12]

Add Pd(II) acetate (635 mg, 2.83 mmol), cataCXium A™ (2.03 g, 5.65 mmol), and aqueous saturated $NaHCO_3$ (186 mL, 188 mmol) to a suspension of 5-bromo-7-methyl-pyrrolo[2,3-d]pyrimidin-4-amine (21.4 g, 94.3 mmol) and 3-methyl-4-(4,4,5,5-tetramethyl-1,3,2-dioxaborolan-2-yl)aniline (28.6 g, 123 mmol) in 2-methyl-tetrahydrofuran (214 mL) at 23° C., and stir the mixture in a sealed tube at 100° C. for 3 h. Cool to 23° C., filter through a pad of diatomaceous earth, and rinse the solid with $H_2O$ (50 mL) and ethyl acetate (100 mL). Separate the organic layer, wash it with aqueous saturated NaCl (50 mL), and concentrate under reduced pressure. Purify the residue by chromatography (eluent: hexane/acetone 0-100%) to obtain the title compound (12.1 g, 51%) as a yellow solid. ES/MS m/z 254.1 (M+H).

Example 1

Synthesis of 2-amino-5-[4-[[(2R)-2-(3,5-difluoro-phenyl)-2-hydroxy-acetyl]amino]-2-methyl-phenyl]-N-isopropyl-pyridine-3-carboxamide

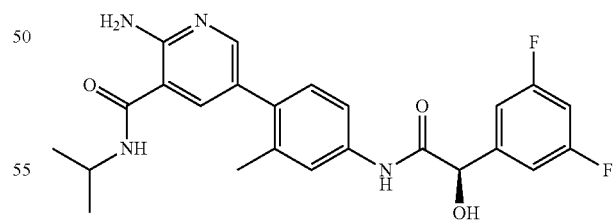

Treat a mixture of (2R)-2-(3,5-difluorophenyl)-2-hydroxyacetic acid (29.0 g, 0.154 mol), 2-amino-5-(4-amino-2-methyl-phenyl)-N-isopropyl-pyridine-3-carboxamide (43.83 g, 0.154 mol), and N,N-diisopropylethylamine (39.8 g, 0.308 mol) in tetrahydrofuran (960 mL), with (1-[bis(dimethylamino)methylene]-1H-1,2,3-triazolo[4,5-b]pyridinium 3-oxid hexafluorophosphate) (87.9 g, 0.231 mol) at 0° C. for 30 min, and then warm to 20° C. and stir for 2 h. Add ethyl acetate (50 mL), and filter the mixture. Concentrate filtrate under reduced pressure, and purify the residue by chromatography (eluent: 2:1 petroleum ether/ethyl acetate) and then by Supercritical Fluid Chromatography, SFC (Column: Chiralpak® IC 30×250 mm 5 μm (Daicel); MeOH/CO$_2$=30:70 isocratic; Flow rate: 80 g/min; Back pressure: 100 Bar; Column temperature: 40° C.) to give the title compound (27.5 g, 39%) as a white solid. ES/MS m/z 455.2 (M+H).

Example 2

Synthesis of 2-amino-5-[4-[[2-(3,5-difluorophenyl)-2-hydroxy-acetyl]amino]-2-methyl-phenyl]-N-isopropyl-pyridine-3-carboxamide

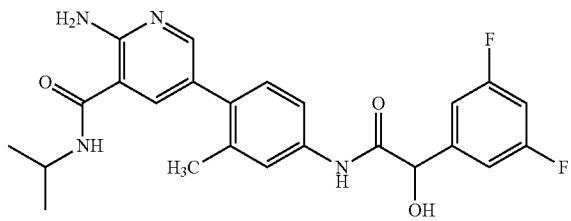 [SMILES: Cc1cc(NC(=O)C(O)c2cc(F)cc(F)c2)ccc1-c1cnc(N)c(C(=O)NC(C)C)c1]

Add 2-amino-5-(4-amino-2-methyl-phenyl)-N-isopropyl-pyridine-3-carboxamide (1000.5 mg, 3.5 mmol) to a solution of 2-(3,5-difluorophenyl)-2-hydroxy-acetic acid (793 mg, 4.2 mmol), (1-[bis(dimethylamino)methylene]-1H-1,2,3-triazolo[4,5-b]pyridinium 3-oxid hexafluorophosphate) (1.7 g, 4.6 mmol), N,N-diisopropylethylamine (909.5 mg, 7.0 mmol) in tetrahydrofuran (7.9 g, 93.6 mol). After 2 hour at room temperature add 3 mL of ethyl acetate and stir reaction for 10 minutes. Filter off the solid and reduce the organic phase under reduced pressure. Wash the residue with saturated aqueous NaHCO$_3$ (10 mL) and extract with DCM (2×10 mL). Dry the organic phase with sodium sulfate, filter and concentrate under reduced pressure.

Purify the residue by HPLC, Rt (retention time)=2.036 minutes (UV), LC Column: XTerra MS C18 (2.1×50 mm, 3.5 um; H$_2$O:Acetonitrile; gradient 0.25 min at 5% B; from 5% B to 100% B in 3 min; stays 0.25 min at 100% B; Column Temp: 50° C.; Flow rate 1.1 mL/min to give the title compound as a mixture of isomer 1 and isomer 2 in a white solid form (0.97 g, 60%). ES/MS (m/z): 455.4 (M+H).

Example 3 and 4

Separation of 2-amino-5-[4-[[2-[3,5-difluorophenyl)-2-hydroxy-acetyl]amino]-2-methyl-phenyl]-N-isopropyl-pyridine-3-carboxamide to isomer 1 and isomer 2

The mixture of isomer 1 and isomer 2 is separated using Chiralcel® OD-H (4.6×100 mm, 5 um), 20% MeOH-DMEA (0.2%) in CO$_2$), 2.5 mL/min, 100 bar Outlet Pressure, 35° C. Temperature to provide individual isomer 1 and isomer 2 as a white solid.

Example 3: 2-Amino-5-[4-[[2-(3,5-difluorophenyl)-2-hydroxy-acetyl]amino]-2-methyl-phenyl]-N-isopropyl-pyridine-3-carboxamide isomer 1. Rt (retention time)=1.131 minutes (430 mg, ee>98%), ES/MS m/z 455.4 (M+H).

Example 4: 2-Amino-5-[4-[[2-(3,5-difluorophenyl)-2-hydroxy-acetyl]amino]-2-methyl-phenyl]-N-isopropyl-pyridine-3-carboxamide isomer 2. Rt (retention time)=1.823 minutes (404 mg, ee>98%), ES/MS m/z 455.4 (M+H)

Example 5

Synthesis of 3-amino-6-[4-[[(2R)-2-(3,5-difluorophenyl)-2-hydroxy-acetyl]amino]-2-methyl-phenyl]-N-methyl-pyrazine-2-carboxamide

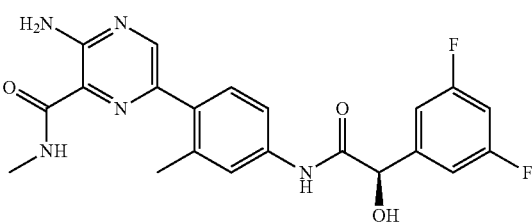 [SMILES: CNC(=O)c1nc(-c2ccc(NC(=O)[C@H](O)c3cc(F)cc(F)c3)cc2C)cnc1N]

Add N,N-(15.3 mL 87.5 mmol) and 1-[bis(dimethylamino)methylene]-1H-1,2,3-triazolo[4,5-b]pyridinium 3-oxid hexafluorophosphate (33.2 g, 87.5 mmol) to a solution of 3-amino-6-(4-amino-2-methylphenyl)-N-methylpyrazine-2-carboxamide (18.0 g, 70.0 mmol) and (2R)-2-(3,5-difluorophenyl)-2-hydroxy-acetic acid (13.2 g, 70.0 mmol) in tetrahydrofuran (90.0 mL), and stir the mixture at 23° C. for 5 h. After this time, concentrate the mixture under reduced pressure, slurry the residue in ethyl acetate (100 mL) for 15 min, filter, and rinse the solid with ethyl acetate (2×25 mL). Concentrate combined filtrates under reduced pressure, and purify the residue by chromatography (eluent: hexane/acetone 2:1, then hexane/ethanol 4:1). Dissolve material in methanol (115 mL), add silica-thiol resin (0.4 g/g), and stir the resulting suspension at 23° C. for 8 h. After this time, filter, and wash the solid with methanol (2×12 mL). Concentrate combined filtrates under reduced pressure. Purify by SFC (Column: Chiralpak® IC 4.6×100 mm 5 μm; 35% methanol (0.2% N,N-dimethylethylamine) in CO$_2$ isocratic; Flow rate: 2.5 mL/min; Back pressure: 100 Bar; Column temperature: 40° C.) to provide the title compound (19.7 g, 62%). ES/MS m/z 428.1 (M+H).

Example 6

Synthesis of 3-amino-6-[4-[[2-(3,5-difluorophenyl)-2-hydroxy-acetyl]amino]-2-methyl-phenyl]-N-methyl-pyrazine-2-carboxamide

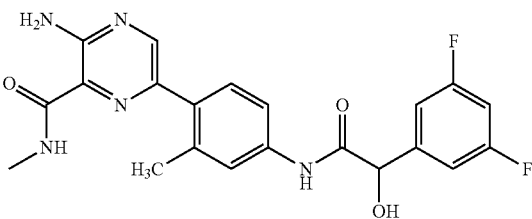 [SMILES: CNC(=O)c1nc(-c2ccc(NC(=O)C(O)c3cc(F)cc(F)c3)cc2C)cnc1N]

Add 3-amino-6-(4-amino-2-methylphenyl)-N-methyl-pyrazine-2-carboxamide (800.0 mg, 3.2 mmol) to a solution of 2-(3,5-difluorophenyl)-2-hydroxy-acetic acid (701.9 mg, 3.4 mmol), (1-[bis(dimethylamino)methylene]-1H-1,2,3-triazolo[4,5-b]pyridinium 3-oxid hexafluorophosphate) (1.7 g, 4.6 mmol), N,N-diisopropylethylamine (803.2 mg, 6.3 mmol) in tetrahydrofuran (7.9 g, 93.6 mol). After 2 hours at room temperature, add 3 mL of ethyl acetate and stir reaction for 10 minutes. Filter off the solid and reduce the organic phase under pressure. Wash the residue with saturated aqueous NaHCO₃ (10 mL) and extract with dichloromethane (2×10 mL). Dry the organic phase with sodium sulfate, filter and concentrate under reduced pressure. Purify the residue by silica gel flash chromatography, eluting with ethyl acetate:hexane (30:70) to give the title compound as a mixture of isomer 1 and isomer 2 in the form of a brown solid (0.72 g, 1.6 mmol). ES/MS (m/z): 428.3 (M+H).

Examples 7 and 8

Separation of 3-amino-6-[4-[[2-(3,5-difluorophenyl)-2-hydroxy-acetyl]amino]-2-methyl-phenyl]-N-methyl-pyrazine-2-carboxamide to isomer 1 and isomer 2

The mixture of isomer 1 and isomer 2 is separated using Chiralpak® OD (4.6×50 mm, 5 um), 20% MeOH-DMEA (0.2%) in CO₂), 5 mL/min, 100 bar Outlet Pressure, 35° C. Temperature to provide individual isomer 1 and isomer 2.

Example 7. 3-Amino-6-[4-[[2-(3,5-difluorophenyl)-2-hydroxy-acetyl]amino]-2-methyl-phenyl]-N-methyl-pyrazine-2-carboxamide isomer 1. Rt (retention time)=1.610 minutes (258 mg, ee>98%), ES/MS m/z 428.3 (M+H).

Example 8. 3-Amino-6-[4-[[2-(3,5-difluorophenyl)-2-hydroxy-acetyl]amino]-2-methyl-phenyl]-N-methyl-pyrazine-2-carboxamide isomer 2. Rt (retention time)=2.410 minutes (278 mg, ee>98%), ES/MS m/z 428.3 (M+H).

Example 9

Synthesis of (2R)-N-[4-(4-amino-7-methyl-pyrrolo [2,3-d]pyrimidin-5-yl)-3-methyl-phenyl]-2-(3-fluorophenyl)-2-hydroxy-acetamide

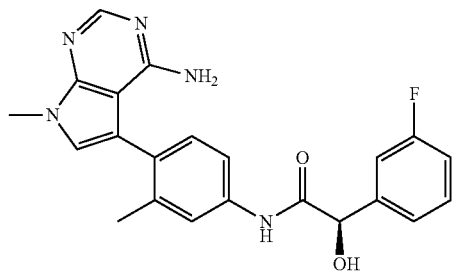 [SMILES: Cc1cc(NC(=O)[C@H](O)c2cccc(F)c2)ccc1-c1cn(C)c2ncnc(N)c12]

Treat a solution of 5-(4-amino-2-methyl-phenyl)-7-methyl-pyrrolo[2,3-d]pyrimidin-4-amine (15.5 g, 44.1 mmol) and (2R)-2-(3-fluorophenyl)-2-hydroxy-acetic acid (8.25 g, 48.5 mmol) in tetrahydrofuran (56 mL) with N,N-diisopropylethylamine (9.22 mL, 52.9 mmol) and 1-[bis (dimethylamino)methylene]-1H-1,2,3-triazolo[4,5-b]pyridinium 3-oxid hexafluorophosphate (20.1 g, 52.9 mmol) at 23° C. for 3.5 h. After this time, concentrate the mixture under reduced pressure, and slurry in ethyl acetate (100 mL) for 15 min. Filter, rinse the solid with ethyl acetate (2×15 mL), and concentrate combined filtrates under reduced pressure. Purify the residue by chromatography (eluent: dichloromethane/methanol 0-10%) and then by SFC (Column size: 5 um, 2×25 cm; Stationary phase-type: 2-Ethylpyridine; Mobile phase-type: CO₂ (A)/methanol-N,N-dimethylethylamine (0.2%) (B); Mobile phase-composition (i.e. A/B ratio): Isocratic 72/25 A/B; Flow rate: 65 mL/min; Loading: 70 mg/4.35 min) to provide the title compound (11.7 g, 65%). ES/MS m/z 406.1 (M+H).

We claim:
1. A compound of formula I:

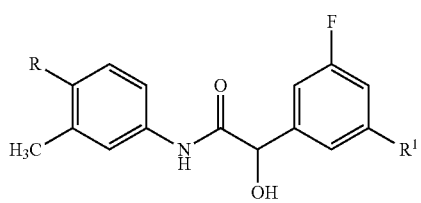

or a pharmaceutically acceptable salt or stereoisomer thereof,
wherein:
R is:

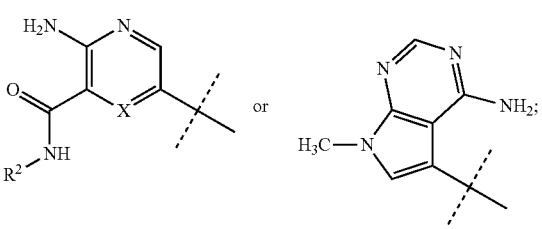

R¹ is H or F;
R² is C₁-C₃ alkyl; and
X is CH or N.

2. The compound of claim 1, wherein the stereoisomer of the compound is of formula Ia:

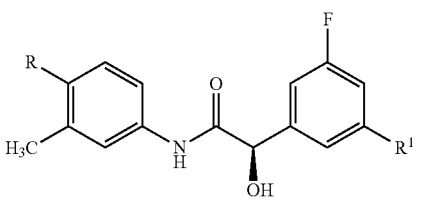

or a pharmaceutically acceptable salt thereof.

3. The compound of claim 1, or a pharmaceutically acceptable salt or stereoisomer thereof, wherein R is:

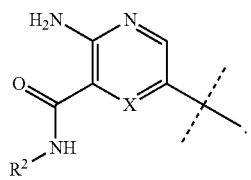

4. The compound of claim 1, or a pharmaceutically acceptable salt or stereoisomer thereof, wherein R² is CH₃ or CH(CH₃)₂.

5. The compound of claim 1, or a pharmaceutically acceptable salt or stereoisomer thereof, wherein R is:

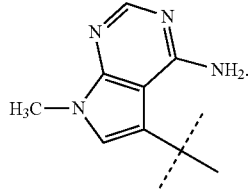

6. The compound of claim 1, wherein the compound is:

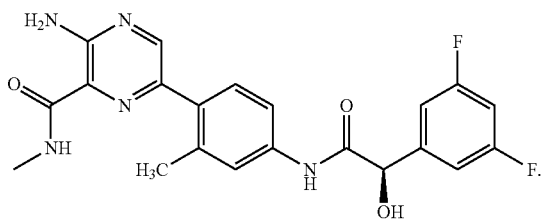 [SMILES: CNC(=O)c1nc(-c2ccc(NC(=O)[C@H](O)c3cc(F)cc(F)c3)cc2C)cnc1N]

or a pharmaceutically acceptable salt thereof.

7. The compound of claim 1, wherein the compound is:

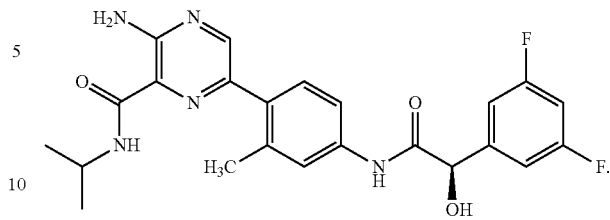

or a pharmaceutically acceptable salt thereof.

8. The compound of claim 1, wherein the compound is:

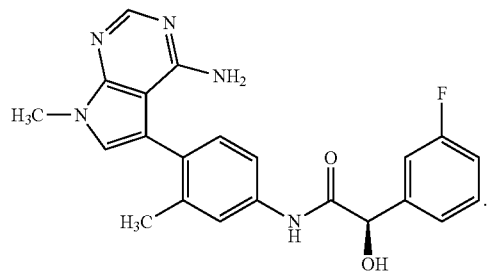 [SMILES: Cc1cc(NC(=O)[C@H](O)c2cccc(F)c2)ccc1-c1cn(C)c2ncnc(N)c12]

or a pharmaceutically acceptable salt thereof.

9. A pharmaceutical composition comprising one or more pharmaceutically acceptable carriers, diluents, or excipients and a compound of claim 1, or a pharmaceutically acceptable salt or stereoisomer thereof.

10. A method for treating pancreatic cancer in a patient, wherein the method comprises administering to the patient in need thereof an effective amount of a compound of claim 1, or a pharmaceutically acceptable salt or stereoisomer thereof.

* * * * *